United States Patent [19]

Roof

[11] 3,981,179

[45] Sept. 21, 1976

[54] FLUID DETECTING SYSTEM

[75] Inventor: Lewis B. Roof, Bartlesville, Okla.

[73] Assignee: Phillips Petroleum Company, Bartlesville, Okla.

[22] Filed: Oct. 15, 1975

[21] Appl. No.: 622,589

[52] U.S. Cl. .......................... 73/61.1 C; 210/198 C
[51] Int. Cl.² ......................................... G01N 31/08
[58] Field of Search ............... 73/61.1 C, 23.1, 19; 23/232 C; 210/24 C, 198 C

[56] References Cited
UNITED STATES PATENTS

| | | |
|---|---|---|
| 3,250,057 | 5/1966 | Clarke ............................ 73/23.1 X |
| 3,427,863 | 2/1969 | Schultz ............................... 73/19 X |
| 3,847,550 | 11/1974 | Scott et al. .................... 73/61.1 C X |
| 3,863,489 | 2/1975 | Ayers et al. .......................... 73/23.1 |

Primary Examiner—Richard C. Queisser
Assistant Examiner—Joseph W. Roskos

[57] ABSTRACT

A system and method wherein a sample fluid in a reference carrier fluid stream is passed through a sample cell to a point of dilution and then through a reference cell, and a detector means indicates a characteristic of the sample fluid by simultaneously comparing at least one identical characteristic of the fluid in the sample cell and the fluid in the reference cell.

13 Claims, 1 Drawing Figure

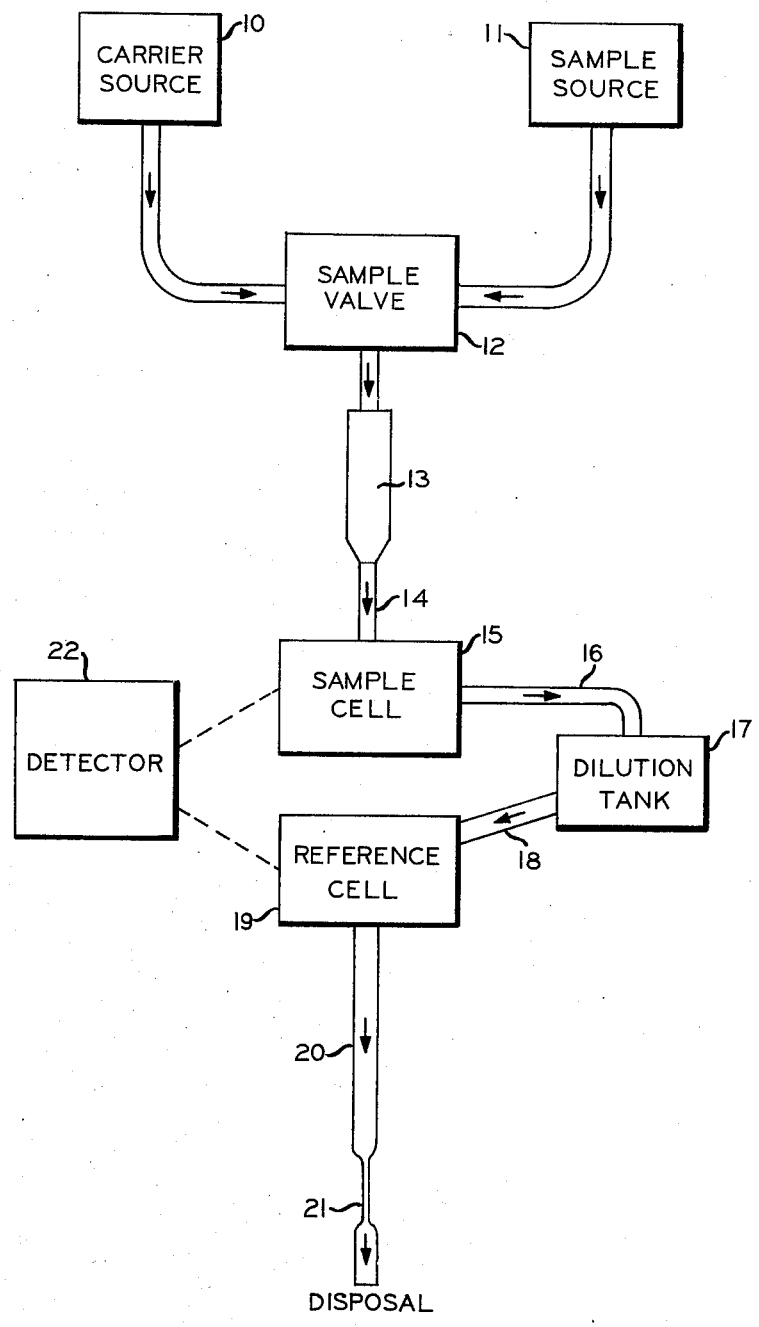

FLUID DETECTING SYSTEM

This invention relates to a fluid detecting system. In another aspect this invention relates to a fluid detecting system wherein a characteristic of a first fluid is compared to a characteristic of a second fluid carrying the first fluid through the fluid detecting system. In another aspect this invention relates to a fluid detecting system used in chromatographic analysis. In yet a further aspect this invention relates to a detecting system used in liquid chromatographic analysis.

A technique often employed in analyzing the constituents of a fluid mixture involves the use of a chromatographic analyzer. In chromatography a sample of material to be analyzed is usually isolated by a sample valve. This isolated portion of sample is then swept by a carrier fluid into a column containing a partitioning material. The various sample components generally have different affinities for the partitioning material. This results in the flowing of sample fluid components through the column at different rates of speed, depending upon their affinities for the partitioning material.

Several known techniques of chromatographic analysis employ a sample cell and a reference cell. The sample cell receives the eluent from the chromatographic column. The eluent comprises carrier fluid or carrier fluid and sample components. The reference cell receives pure carrier fluid. A characteristic of a sample component in the sample cell is then determined by employing a detector means capable of comparing differences in a characteristic of the fluid in the reference cell and the fluid in the sample cell. Examples of such detector means often employed in chromatographic systems include refractive index detectors, ultraviolet detectors, and dielectric type detectors.

In conventional chromatographic systems the carrier fluid for the reference cell is supplied by means separate from those employed for providing the carrier fluid which carries the sample through the chromatographic column and into the sample cell. In using different pumps, valves, restrictors, and/or piping to provide carrier fluids to the reference cell and to the sample cell it is sometimes difficult to prevent variations in pressure, flow rates, or temperatures of the fluids going into the respective cells. When such variations occur, the detector's comparison of the characteristic of the fluids in the sample cell and the reference cell may not provide an accurate measure of the characteristic of the sample fluid in the sample cell.

Therefore an object of this invention is to provide a liquid detecting system wherein separate means are not needed to provide carrier fluid to the sample cell and the reference cell.

Another object of this invention is to provide a detecting system which reduces the amount of carrier fluid which must be employed.

A further object is to provide for a liquid chromatographic system, a detecting system having less tendency to have fluctuations in flow or pressure which would affect the ability of the detector to provide a proper measure of a characteristic of the sample component.

A further object is to provide a method for conducting liquid chromatography without the necessity of having separate pumps and/or lines for the carrier fluid which carries sample to the sample cell and the fluid which is employed as a reference in the reference cell.

The detecting system of this invention comprises a sample cell, a reference cell, a dilution tank, and a detector means. Both the sample cell and the reference cell are adapted to enable the detector means to compare at least one characteristic of the fluid contained in each cell. The sample cell has an inlet through which sample and carrier fluids can flow from a source of supply. The sample cell has an outlet which is connected to the inlet of a dilution tank. The dilution tank, in turn, has an outlet which is connected to the inlet of the reference cell. The reference cell has an outlet which allows fluid from the dilution tank to flow through said reference cell to some point of disposal or recovery. The dilution tank is of such size that after it has been filled with carrier fluid any sample fluid component coming from the sample cell will in the tank become so diluted in carrier fluid that its presence in the carrier fluid which passes from the dilution tank into the reference cell will be so small that the detector's comparison will not be significantly affected by it. Thus the sample fluid component passing into the reference cell will be so diluted that its concentration is below the detector's ability to measure it. In other words, any sample component in the carrier fluid entering the reference cell will be so diluted that the detector will be affected as if only carrier fluid were present.

When the carrier fluid employed is a liquid it is advantageous to include in the outlet of the reference cell a means which restricts flow so that a pressure can be maintained in the cells such that bubbles are not formed due to gas in the carrier fluid.

The drawing is a schematic representation of a chromatographic system employing a detecting system within the scope of this invention.

Referring now to the drawing, a carrier fluid source 10 and a sample fluid source 11 are connected to a sample valve 12. The sample valve 12 is adapted to trap a particular volume of sample, then allow carrier fluid from the carrier source 10 to force that sample portion from the valve and through the chromatographic column 13. An example of a valve capable of performing such a function is provided by U.S. Pat. No. 2,846,121.

Eluent from the chromatographic column 13 is passed through conduit means 14 to a sample cell 15. The fluid from the sample cell 15 then passes through conduit means 16 into a dilution tank 17. The dilution tank 17 is of such size that after being filled with carrier fluid any sample fluid component flowing through conduit means 16 into the dilution tank will therein become so diluted with carrier fluid that the amount of sample fluid component present in carrier fluid flowing from the dilution tank 17 through conduit means 18 to the reference cell 19 will be so small that the detector's comparison will not be significantly affected by the presence of sample fluid in the reference cell.

Reference cell 19 and sample cell 15 are both adapted to enable the detector means 22 to compare at least one identical characteristic of the fluid contained in each. This includes any system in which the sample cell 15, reference cell 19, and detector means 22 are so arranged and adapted that the detector means is capable of reflecting a characteristic of a sample component in the sample cell by comparing at least one characteristic of the fluids in each of the cells. For example, a refractive index detector can provide a comparison by observing the position of a light beam that has been passed through adjacent sample and reference cells and then reflected back through the adjacent cells to a light-sensitive means in the detector means. Another example of a detector falling within the scope of this invention is an ultraviolet detector wherein a dual photocell means senses the difference between the ultraviolet absorption characteristics of the fluids in the sample and reference cells.

The reference cell 19 is provided with an outlet conduit means 20 which directs fluid from the reference cell to a point of disposal or recovery. Conduit means 20 can contain a restrictor 21 which is beneficial when the carrier fluid is a liquid. Due to the presence of the restrictor 21 the flow of fluid out of the detector system is restricted in such a manner as to minimize the possibility of the formation of bubbles in either the reference cell or the sample cell. The formation of bubbles in either cell could have adverse effects upon the reliability of the comparison obtained by the detector.

Although the essence of this invention can be applied to other systems in which a detector means is employed to compare at least one characteristic of fluids in a reference cell and a sample cell, the detector system of this invention is particularly useful in liquid chromatographic analysis. In a typical liquid chromatographic system the sample valve 12 is generally constructed so that it can isolate a 2–15 microliter sample which can be directed to the column 13. The column 13 is generally 0.1–4 meters in length, 2–15 millimeters in internal diameter, and packed with a partitioning material such as spherical or irregular beads 5–75 micrometers in diameter. The tubings and fittings in the flow path between the sample valve 12 and the sample cell 15 have minimal volume so that peak spread in the tube is minimized. Typically such tubing has an internal diameter of about 0.01 inch (0.03 centimeters). The carrier liquid flow rate typically employed in such a chromatographic system is on the order of 1 cc/hr.

As indicated above, according to this invention, the dilution tank in the detecting system must be of such size that any sample component entering it will become so diluted with carrier fluid that the detector will be affected as if only pure carrier fluid were present when the fluid in the tank passes through the reference cell. For the detectors employed with most liquid chromatographs it is generally sufficient if the dilution tank has a volume in the range of about 1000 to about 100,000 times the volume of the sample isolated by the sample valve. Preferably the volume of the dilution tank is from about 10,000 to about 75,000 times the volume of the sample introduced into the chromatography column. Thus when the sample valve of a liquid chromatographic system provides a 2–15 microliter sample as described above, a tank having a volume of about 150 cubic centimeters is sufficient for the dilution tank employed in the system of this invention.

In a liquid chromatographic system as described thus far, the detecting system's tubing, represented in the drawing by conduit means 16, 18, and 20, generally will have an inside diameter of from about ⅛ inch (0.3 cm) to about 1/16 inch (0.15 cm). Basically, however, this tubing can be of any size which is compatible with the efficiency and reproducibility of the objectives desired in the chromatographic system.

Generally in a chromatographic system as just described, the pressures upstream of the column 13 are in the range of about 1000 to about 5000 psig. To prevent the formation of bubbles in the sample or reference cells due to dissolved gases in the liquids flowing through the system, it has been found desirable to employ a restrictor 21 in conduit means 20 that is designed so the pressures in the sample and reference cells will be maintained high enough to prevent the gases dissolved in the fluids from forming bubbles. Generally when the pressure above the column is in the range of about 1000 to about 5000 psig, it is preferred that the restrictor be capable of maintaining the pressure in the sample cell and the reference cell at a substantially identical level in the range of about 5 to 50 psig.

In employing a liquid chromatographic system as described above in the analysis of a sample liquid, it is necessary as a preliminary step to analysis, to pass a sufficient amount of carrier through the column to fill at least the column 13, sample cell 15, reference cell 19, and dilution tank 17. Thereafter, the chromatographic column 13 is operated in a conventional manner. For example, the sample valve 12 is operated to obtain a small amount of sample liquid, which amount preferably is sufficient to insure that the sample components entering the sample cell 15 after separation in the chromatographic column 13 will be reflected in the detector's comparison of the liquids in the sample cell 15 and the reference cell 19.

This isolated portion of sample liquid is then carried into the column 13 with enough carrier liquid to drive various sample components through the column 13 and into the sample cell 15. Then the detector 22 simultaneously compares at least one characteristic of the fluid in the sample cell 15 and the fluid in the reference cell 19 as the fluids pass therethrough.

Although not included in the schematic representation provided by the drawing, heat controls, pressure controls, housings, etc., used to stabilize conventional liquid chromatographs can also be employed with a liquid chromatograph employing the liquid detecting system of this invention. It is intended that all matter contained in the above description or shown in the accompanying drawing shall be interpreted as illustrative and not in a limitative sense.

What is claimed is:

1. A fluid detecting system comprising a sample cell having an inlet and an outlet, a means capable of providing sample fluid and carrier fluid to the inlet of said sample cell, a dilution tank having an inlet and an outlet, a means capable of providing fluid communication between said sample cell outlet and said dilution tank inlet, a reference cell having an inlet and outlet, a means capable of providing fluid communication between said dilution tank outlet and said reference cell inlet, and a detector means adapted to compare at least one characteristic of the fluids in the sample cell with the same characteristic of the fluids in the reference cell, wherein said dilution tank is of such size that after said dilution tank has been filled with carrier fluid any sample fluid component coming from the sample cell will in said dilution tank become so diluted with carrier that the detector means comparison will not be significantly affected by the level of sample fluid component in the fluids in said reference cell.

2. A fluid detecting system according to claim 1 wherein said outlet from said reference cell contains a restrictor means which restricts the flow out of the detecting system in such a manner as to maintain pressure in the cells to prevent the formation of bubbles in either the reference cell or the sample cell when the detecting system is in operation.

3. A fluid detecting system according to claim 2 wherein the source of sample and carrier fluid is a liquid chromatographic column.

4. A fluid detecting system according to claim 3 wherein the dilution tank is from about 1000 to about 100,000 times greater in volume than the volume of the sample to be separated in the liquid chromatographic column.

5. A fluid detecting system according to claim 4 wherein said restrictor in said reference cell outlet is capable of maintaining the pressure in said sample cell and said reference cell at a substantially identical level in the range of 5 to 50 psi when the pressure upstream of the liquid chromatographic column is in the range of 1000 to 5000 psi.

6. A fluid detecting system according to claim 5 wherein the liquid chromatographic column is 0.1 to 4 meters in length, 2 to 5 millimeters in internal diameter, and packed with spherical or irregular beads 5 to 75 micrometers in diameter, and the sample fluid is provided for the column by way of a sample valve adapted to trap a 2 to 15 microliter sample and to use the flow of carrier fluid to carry said sample into said column, the tubings and fittings in the flow path between said sample valve and said column and between said column and said sample cell having such small volume that peak spreading in that flow path is minimal.

7. A fluid detecting system according to claim 6 wherein the dilution tank has a volume of about 150 cubic centimeters.

8. A fluid detecting system according to claim 3 wherein the dilution tank has a volume of from about 10,000 to about 75,000 times the volume of sample to be separated in the liquid chromatographic column.

9. A process for the analysis of a fluid stream which is predominately a carrier fluid containing at least one other fluid component in amounts that can be detected by the detector employed in the analysis comprising filling a first detection zone and a second detection zone with said aforementioned carrier fluid containing no amounts of other substances which can be detected by the detector being employed, then passing the fluid to be analyzed through said first detection zone, passing the fluid from said first detection zone to a dilution zone, passing the thus diluted fluid from the dilution zone through said second detection zone, the fluid being diluted with said carrier fluid in said dilution zone until only said carrier fluid is detectable in said second detector zone by the detector being employed, and comparing at least one characteristic of the fluids in the two detection zones as the fluid to be analyzed is passed through said first detection zone.

10. A process according to claim 9 wherein the dilution of the fluid coming from said first detection zone is accomplished by passing said fluid from said first detection zone into a dilution zone containing an amount of said carrier fluid such that if the noncarrier component, that is the total fluid component in the amount of said fluid stream analyzed other than the carrier fluid component, were combined with the amount of carrier fluid in the dilution zone, said noncarrier component of said fluid stream would be so diluted that the detector employed would not be significantly affected by the presence of noncarrier component in the fluid passing into the second detection zone.

11. A process according to claim 10 wherein the amount of carrier fluid in dilution zone is from 1000 to 100,000 times the volume of noncarrier component contained in the amount of the fluid stream that is subjected to analysis.

12. A process according to claim 11 wherein the fluid stream that is analyzed is the eluent from a chromatographic column.

13. A process according to claim 12 wherein the fluid stream that is analyzed is a liquid eluent from a liquid chromatographic column.

* * * * *